(12) United States Patent
Kaneko

(10) Patent No.: US 11,844,803 B2
(45) Date of Patent: Dec. 19, 2023

(54) RENAL DYSFUNCTION IMPROVING DRUG COMPRISING OPTICAL ISOMER OF 1,4-BENZOTHIAZEPINE-1-OXIDE DERIVATIVE

(71) Applicants: AETAS PHARMA CO., LTD., Tokyo (JP); Noboru Kaneko, Oyama (JP)

(72) Inventor: Noboru Kaneko, Oyama (JP)

(73) Assignees: AETAS PHARMA CO., LTD., Tokyo (JP); Noboru Kaneko, Oyama (JP)

( * ) Notice: Subject to any disclaimer, the term of this patent is extended or adjusted under 35 U.S.C. 154(b) by 0 days.

(21) Appl. No.: 16/771,877

(22) PCT Filed: Dec. 11, 2018

(86) PCT No.: PCT/JP2018/045416
§ 371 (c)(1),
(2) Date: Jun. 11, 2020

(87) PCT Pub. No.: WO2019/117116
PCT Pub. Date: Jun. 20, 2019

(65) Prior Publication Data
US 2020/0390782 A1    Dec. 17, 2020

(30) Foreign Application Priority Data
Dec. 11, 2017   (JP) .................. 2017-236833

(51) Int. Cl.
*A61K 31/554*   (2006.01)
*A61P 13/12*   (2006.01)

(52) U.S. Cl.
CPC ............ *A61K 31/554* (2013.01); *A61P 13/12* (2018.01)

(58) Field of Classification Search
CPC ............. A61K 31/554; A61P 9/06; A61P 9/10
(Continued)

(56) References Cited

U.S. PATENT DOCUMENTS

| 5,416,066 A | 5/1995 | Kaneko et al. |
| 6,506,745 B1 | 1/2003 | Aisaka et al. |

(Continued)

FOREIGN PATENT DOCUMENTS

| EP | 2402333 A1 | 1/2012 |
| EP | 3176164 A1 | 6/2017 |

(Continued)

OTHER PUBLICATIONS

Cole et al. "Renal dysfunction in hear Failure," Med. Clin. N. Am. vol. 96, 2012, 955-974 (Year: 2012).*

(Continued)

*Primary Examiner* — Shengjun Wang
(74) *Attorney, Agent, or Firm* — WHDA, LLP

(57) ABSTRACT

The present invention addresses the problem of providing a pharmaceutical composition for treatment of a variety of conditions accompanied by renal dysfunction.
Renal dysfunction is improved by a pharmaceutical composition that comprises an optical isomer of a 1,4-benzothiazepine-1-oxide derivative represented by general formula [II]

[II]

(Continued)

wherein, R represents a hydrogen atom or a hydroxyl group, and "*" indicates being an optical isomer.
or a pharmacologically acceptable salt thereof.

5 Claims, 5 Drawing Sheets

(58) Field of Classification Search
USPC .................................................. 514/211.09
See application file for complete search history.

(56) References Cited

U.S. PATENT DOCUMENTS

| | | | |
|---|---|---|---|
| 2007/0219180 | A1 | 9/2007 | Kaneko |
| 2011/0306594 | A1 | 12/2011 | Kaneko et al. |
| 2017/0247362 | A1* | 8/2017 | Kaneko .................... A61P 9/00 |

FOREIGN PATENT DOCUMENTS

| | | | |
|---|---|---|---|
| JP | 2000-247889 | A | 9/2000 |
| JP | 2001-31571 | A | 2/2001 |
| JP | 2003-95977 | A | 4/2003 |
| JP | 4808825 | B2 | 11/2011 |
| WO | 92/12148 | A1 | 7/1992 |
| WO | 2005/105793 | A1 | 11/2005 |
| WO | 2010/098080 | A1 | 9/2010 |
| WO | 2010/114562 | A1 | 10/2010 |
| WO | 2010/114563 | A1 | 10/2010 |
| WO | 2016/017448 | A1 | 2/2016 |

OTHER PUBLICATIONS

Maisel et al. "Atrial fibrillation in heart failure: Epidemiology, pathophysiology, and rationale for therapy," The American J. Cardiology, 2003, vol. 91, 6A, 2D-8D. (Year: 2003).*

Extended (Supplementary) European Search Report dated Jul. 9, 2021, issued in counterpart EP Application No. 18887948.0. (8 pages).

Lisy, et al., "New Cardioprotective Agent K201 Is Natriuretic and Glomerular Filtration Rate Enhancing", Circulation, 2006, vol. 113, No. 2, pp. 246-251, ISSN 0009-7322, abstract, fig. 3, cited in ISR (6 pages).

International Search Report dated Jan. 29, 2019, issued in counterpart International Application No. PCT/JP2018/045416 (1 page).

Adams, et al., "Characteristics and outcomes of patients hospitalized for heart failure in the United States: Rationale, design, and preliminary observations from the first 100,000 cases in the Acute Decompensated Heart Failure National Registry (ADHERE)", American Heart Journal, 2005, vol. 149, No. 2, pp. 209-216, cited in Specification, (8 pages).

Askoxylakis, et al., "Long-term survival of cancer patients compared to heart failure and stroke: A systematic review", BMC Cancer, 2010, vol. 10, No. 105, cited in Specification, (8 pages).

Starns, et al., "Effects of K201 on repolarization and arrhythmogenesis in anesthetized chronic atrioventricular block dogs susceptible to dofetilide-induced torsade de pointes", European Journal of Pharmacology, 2011, vol. 672, pp. 126-134, cited in Specification, (9 pages).

* cited by examiner

RENAL DYSFUNCTION IMPROVING DRUG COMPRISING OPTICAL ISOMER OF 1,4-BENZOTHIAZEPINE-1-OXIDE DERIVATIVE

TECHNICAL FIELD

The present invention relates to a pharmaceutical composition for improving renal dysfunction comprising an optical isomer of a 1,4-benzothiazepine-1-oxide derivative or a pharmaceutically acceptable salt thereof.

BACKGROUND ART

Kidneys are organs located on the right and left dorsal lumbar parts and the kidney weight in an adult human is approximately 130 g. Main functions of the kidneys are 1) to maintain the total body fluid volume, 2) to excrete waste such as urea nitrogen or creatinine, and 3) to maintain the homeostasis of an electrolyte such as sodium (Na), potassium (K), chlorine (Cl), or phosphorus (P) in the living body, by generation and excretion of urine.

In the kidney, there are many structures called glomeruli (nephrons), which are spherical forms of blood vessels about having almost the same thickness as that of the capillaries, forming a yarn ball shape. Approximately a million glomeruli exist in one kidney, form complicated anastomoses in the glomeruli, and have a size of approximately 0.1 mm in diameter.

The functions of the glomeruli are to filter water, wastes such as creatinine and urea nitrogen, and electrolytes, or the like from the blood. For these filtered substances, water and electrolytes or the like are reabsorbed or re-secreted in the proximal tubule, distal tubule, and collecting tubule following the glomeruli according to the needs of the body, and creatinine and urea nitrogen or the like, which are unnecessary wastes in the living body, are excreted as urine. The kidneys are responsible for maintaining certain concentrations of these substances in the living body and maintaining the biological environment through proper excretion.

A main cause for the renal dysfunction is a decrease in glomerular filtration rate, and the decrease in filtration rate brings about an increase in blood creatinine or urea nitrogen and an increase in potassium level in the living body.

The renal dysfunction is classified, on the basis of the duration of disease, into an acute disease in which the duration of disease is shorter than 3 months of onset (hereinafter, also referred to as "acute kidney disease") and a chronic disease in which the duration of disease is 3 months or longer (hereinafter, also referred to as "chronic kidney disease"). As for the chronic kidney disease, a chronic kidney disease caused by diabetic renal disorder (diabetic nephropathy) most often occurs in accordance with an increase in the number of patients with diabetes in recent years. A chronic kidney disease caused by chronic glomerulonephritis secondarily often occurs.

The acute kidney disease is further classified, on the basis of the site of origin thereof, into prerenal, nephrogenic, and postrenal acute kidney diseases. The prerenal acute kidney disease is renal dysfunction developed by decreasing a blood flow rate to the kidneys due to bleeding, severe drop in blood pressure (such as shock), or the like. If the renal artery constricts due to arteriosclerosis, renal dysfunction caused by renal ischemia occurs. In addition, congestion occurs in the kidney even due to heart failure and this congestion causes renal dysfunction. The nephrogenic acute kidney disease is dysfunction of glomeruli themselves. This nephrogenic acute kidney disease is caused by renal parenchymal dysfunction due to acute glomerulonephritis or a drug (for example, anticancer agents or antibiotics). The postrenal Acute kidney disease is caused by increased internal pressure in glomeruli and renal tubules from inhibition of urinary drainage due to prostatic hypertrophy or urinary tract obstruction, resulting in renal dysfunction.

The diseases accompanied by renal dysfunction are also classified, on the basis of pathological conditions or affected regions thereof, into glomerular diseases, tubulointerstitial diseases, kidney failure, nephropathy, polycystic kidney diseases, and the like. The glomerular diseases include diseases accompanied by glomerular dysfunction such as acute nephritic syndrome, rapidly progressive glomerulonephritis syndrome, recurrent or persistent hematuria, chronic nephritic syndrome, and nephrotic syndrome. The tubulointerstitial diseases include diseases accompanied by renal tubulointerstitial damage such as tubulointerstitial nephritis (acute, chronic, or unspecified tubulointerstitial nephritis). The kidney failure includes acute kidney failure and chronic kidney failure. The nephropathy includes virus-associated nephropathy (HB virus-associated nephropathy, HC virus-associated nephropathy, HIV-associated nephropathy, BK virus-associated nephropathy, or the like), renal sarcoidosis, diabetic nephropathy, hereditary nephropathy, familial nephritis, hypertensive nephropathy, hepatorenal syndrome, NSAID nephropathy, analgesic nephropathy, contrast-induced nephropathy, heavy metal-induced nephropathy, and the like.

If the renal dysfunction occurs, the glomerular filtration rate is decreased, and as a result, an increase in blood creatinine and urea nitrogen occurs. If the renal dysfunction becomes heavier, the excretion of blood potassium (K) is impaired so that a serum K level is increased. An increase in blood K can lead to life-threatening arrhythmia such as ventricular fibrillation. In the renal dysfunction, sodium (Na) excretion is also impaired. An increase in blood Na causes an increase in amount of circulating blood so that edema occurs throughout the body. In this case, as a pharmaceutical agent improving edema, for example, a loop diuretic or thiazide diuretic that promotes Na excretion to increase the urine volume by inhibiting Na reabsorption in renal tubule is used. Further, a potassium-conserving diuretic that promotes diuresis by blocking aldosterone in renal tubule is also used in clinical practice. However, these pharmaceutical agents have no action of excreting waste such as creatinine or urea nitrogen. Furthermore, since the loop diuretic or thiazide diuretic has no action of improving the renal function, and conversely, degrades the renal function, the loop diuretic or thiazide diuretic cannot be administered in patients with severe renal dysfunction.

It has been reported that 60% of males and 90% of females of patients with heart failure have complication of renal dysfunction (Non-Patent Document 1). If heart failure occurs, edema occurs throughout the body, and as a therapeutic agent for edema, a loop diuretic or a thiazide diuretic is used. However, these diuretics further interfere the renal function, so that the renal dysfunction complicated by heart failure becomes severe and patient's prognosis becomes poor. It has been reported that the prognosis of a patient with heart failure is poorer than that of patient with general "cancers" (excluding pancreatic cancer or the like) (Non-Patent Document 2). As described above, the renal dysfunction is deeply involved with the prognosis of the patient with heart failure so that it is desired to develop a novel diuretic improving the renal dysfunction.

Since there is no pharmaceutical agent that increases a glomerular filtration rate and decreases blood creatinine or the like, it is a current situation in the treatment of the renal dysfunction that a conservative medical treatment, which does not impose a burden to kidneys as much as possible, such as 1) constraint on excessive intake of water, 2) constraint on intake of dietary salt (NaCl), 4) constraint on intake of potassium salt (K), 5) constraint on intake of protein, 6) stabilization of blood pressure (hypertension increases an intraglomerular pressure, and as a result, the renal disorder is promoted) and 6) prevention of dehydration, is performed. However, since the effect of the conservative medical treatment is limited and waste such as creatinine or urea nitrogen cannot be sufficiently excreted, kidney failure (renal dysfunction G5 described below) finally may occur and dialysis or kidney transplantation may be forced to be performed.

The prognosis of a patient with renal dysfunction is resolved/cured in a half of patients in the case of the acute kidney disease if causes thereof are eliminated. In contrast, in the chronic kidney disease, there is no pharmaceutical agent improving the renal dysfunction, and thus, although varying among different individuals, the chronic kidney disease becomes severe over time in many cases. Moreover, age-related renal arteriosclerosis also deteriorates the renal function, and thus the renal dysfunction is likely to proceed gradually with advancing age. If the renal dysfunction finally becomes G5, dialysis treatment is forced to be performed unless kidney transplantation is performed. Currently, the number of patients receiving dialysis is considered to be approximately 300,000 in Japan. Dialysis has not only a therapeutic problem but also becomes a serious social problem such as human loss or economic loss since it takes a lot of medical expenses in the course of the year. In the future, with the aging of the population and an increase in the number of patients with diabetes, development of drugs improving renal function becomes an urgent issue. Currently, since there is no pharmaceutical agent decreasing serum creatinine, a pharmaceutical agent decreasing serum creatinine will be a revolutionary pharmaceutical agent for patients with renal dysfunction.

The present inventors have hitherto conducted studies on 4-[3-(4-benzylpiperidin-1-yl)propionyl]-7-methoxy-2,3,4,5-tetrahydro-1,4-benzothiazepine and a derivative thereof (see Patent Document 1 and 2) and have reported the compound. Further, for example, it has been found and reported that the compound has an action of promoting the effect of carcinostatic agents (see Patent Document 3) or an action of inhibiting the leak of $Ca^{2+}$ from the sarcoplasmic reticulum by amelioration and/or stabilization of ryanodine receptor function (see Patent Document 4), the compound is useful as a muscle relaxation accelerator, a therapeutic agent for left ventricular diastolic dysfunction, a therapeutic agent for angina pectoris, a therapeutic agent for acute pulmonary edema, a blood ameliorant for microcirculation system, a therapeutic agent for hypertension, a therapeutic agent for ventricular tachycardia, a therapeutic agent for Torsades de Pointes, or the like (see Patent Document 5), and the like. However, regarding a compound JTV519 (also called K201 and being a compound corresponding to a compound [III] in the present specification) that belongs to the 4-[3-(4-benzylpiperidin-1-yl)propionyl]-7-methoxy-2,3,4,5-tetrahydro-1,4-benzothiazepine and the derivative thereof, it has been reported that when 1.2 mg/kg body weight of JTV519 is administered to a dog with complete atrioventricular block, Torsades de Pointes that is life-threatening arrhythmia occurs (Non-Patent Document 3). Therefore, JTV519 (K201) cannot be applied directly in a clinical setting to humans.

In addition, the present inventors have found and reported that 1,4-benzothiazepine-1-oxide derivative having the following formula [I], which is typified by 4-[3-(4-benzylpiperidin-1-yl)propionyl]-7-methoxy-2,3,4,5-tetrahydro-1,4-benzothiazepine-1-oxide corresponding to one of oxides of the above-described compound, is also useful as a therapeutic or prophylactic agent for myocardium relaxation disorder that is observed in atrial arrhythmia as well as for heart failure or hypertension, diastolic dysfunction, angina pectoris or myocardial infarction, hypertensive disease, or ischemic heart disease, heart failure, and ventricular arrhythmia (see Patent Document 6).

[Chemical Formula. 1]

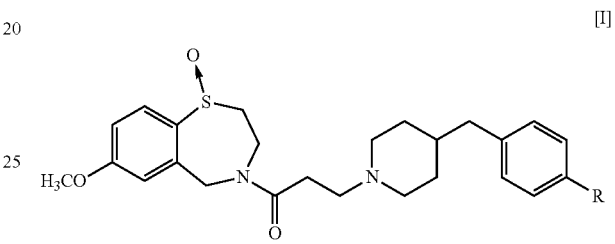

[I]

wherein, R represents a hydrogen atom or a hydroxyl group.

In Patent Document 6, the improving action of the heart function is described, but the improving action of the renal function as the action of the compound is not described.

Meanwhile, in a 1,4-benzothiazepine-1-oxide derivative having the following formula [II], the sulfur atom in the S-oxide part is a chiral center so that the derivative has central chirality.

[Chemical Formula. 2]

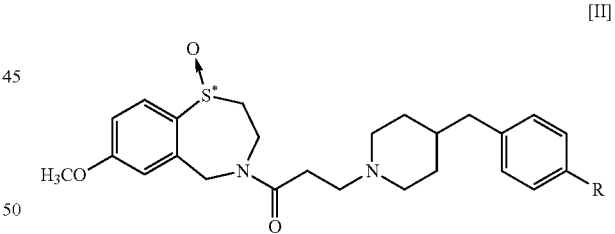

[II]

wherein, R represents a hydrogen atom or a hydroxyl group, and "*" indicates the presence of optical isomers.

Regarding 4-[3-(4-benzylpiperidin-1-yl)propionyl]-7-methoxy-2,3,4,5-tetrahydro-1,4-benzothiazepine-1-oxide that is one of the compounds having the formula [II], the present inventors have been tried to separate stereoisomers related to the central chirality, and as a result, stable separation can be achieved even at 40° C., and thus the present inventor has succeeded in isolating each enantiomer (Patent Document 7). In the present specification, similarity to Patent Document 7, between two enantiomers that are separated by the present inventors by using a chiral column, the first eluted enantiomer is referred to as a first component (or also referred to as a compound (A) in some cases), and the next eluted enantiomer is referred to as a second component (or also referred to as a compound (B) in some cases). The ratio of amounts of the separated first component and second component was approximately 1:1. Next, the present inventors have collected each of the two enantiomers (hereinafter, also referred to as optical isomers).

Furthermore, as a result of determining the pharmacological activity of both of them, it has been found that the first optical isomer component (compound (A)) and the second optical isomer component (compound (B)) have a contradictory action so that, regarding atrial fibrillation in particular, only the first component has a very specific pharmaceutical activity from which a high anti-atrial fibrillation effect and an effect of lowering proarrhythmic potential can be expected (Patent Document 7). However, also as for both the optical isomers, the improving action of the renal function is not described as the action thereof. Incidentally, through crystal structure analysis, it is confirmed that the first component is an (R) form and the second component is an (S) form.

CITATION LIST

Patent Document

Patent Document 1: WO 92/12148 A1
Patent Document 2: JP 2000-247889 A
Patent Document 3: JP 2001-31571 A
Patent Document 4: JP 2003-95977 A
Patent Document 5: WO 2005/105793 A1
Patent Document 6: JP 4808825 B2
Patent Document 7: WO 2016/017448 A1

Non-Patent Document

Non-Patent Document 1: Am. Heart J., 2005; 149(2):209-216
Non-Patent Document 2: BMC Cancer, 2010; 10:105
Non-Patent Document 3: Eur. J. Pharmacol., 2011; 672(1-3):126-134

SUMMARY OF THE INVENTION

Problems to be Solved by the Invention

An object of the present invention is to provide a pharmaceutical composition which has actions of increasing the urine volume, increasing the amount of urinary sodium, increasing the amount of urinary potassium, and/or decreasing the amount of serum creatinine and is useful for improving renal dysfunction.

Means for Solving the Problems

The present inventors have conducted intensive studies on various pharmacological actions of a 1,4-benzothiazepine-1-oxide derivative having the following formula [I]:

[Chemical Formula. 1]

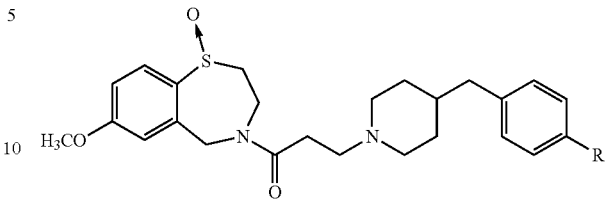

[I]

wherein, R represents a hydrogen atom or a hydroxyl group.

As a result, the present inventors have found that an optical isomer (compound (A)), which is an optically active 1,4-benzothiazepine-1-oxide derivative having the following formula [II] and is one of optically active 4-[3-(4-benzylpiperidin-1-yl)propionyl]-7-methoxy-2,3,4,5-tetrahydro-1,4-benzothiazepine-1-oxide, has an improving action of renal dysfunction, that is, remarkable actions of increasing the urine volume, promoting blood creatinine excretion in addition to Na excretion and K excretion, and decreasing blood creatinine with a low dosage, thereby completing the present invention.

[Chemical Formula. 2]

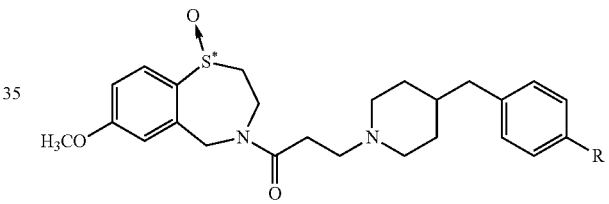

[II]

wherein, R represents a hydrogen atom or a hydroxyl group, and "*" indicates the presence of optical isomers.

That is, the present invention relates to a pharmaceutical composition comprising an optical isomer of a 1,4-benzothiazepine-1-oxide derivative having the following formula [II] or a pharmaceutically acceptable salt thereof:

[Chemical Formula. 2]

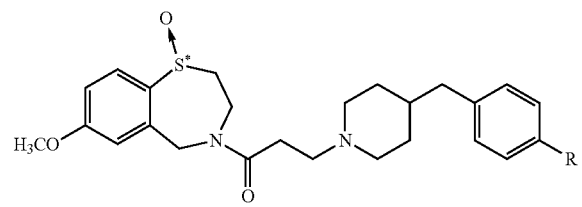

[II]

wherein, R represents a hydrogen atom or a hydroxyl group, and "*" indicates the presence of optical isomers.

More specifically, the present invention relates to a pharmaceutical composition comprising a first optical isomer component of the 1,4-benzothiazepine-1-oxide derivative having the above formula [II] or a pharmaceutically acceptable salt thereof. The pharmaceutical composition of the present invention has actions of increasing the urine volume, increasing the amount of urinary sodium, increasing the amount of urinary potassium, and/or decreasing the amount of serum creatinine, is useful for improving renal dysfunction, and can be used in treatment of a variety of conditions accompanied by renal dysfunction.

The present invention will be described in more detail as follows.

(1) A pharmaceutical composition for improving renal dysfunction comprising:

an optical isomer of a 1,4-benzothiazepine-1-oxide derivative having the following formula [II] or a pharmaceutically acceptable salt thereof, and a pharmaceutically acceptable carrier:

[Chemical Formula. 2]

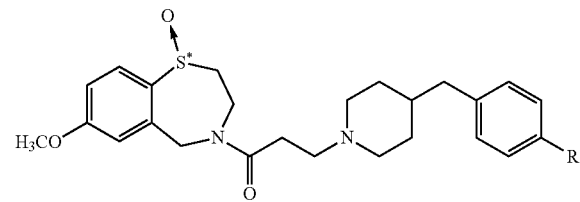

[II]

wherein, R represents a hydrogen atom or a hydroxyl group, and "*" indicates the presence of optical isomers.

(2) The pharmaceutical composition described in the above (1), wherein improvement in renal dysfunction is a decrease in a serum creatinine value.

(3) The pharmaceutical composition described in the above (1) or (2), wherein improvement in renal dysfunction is an increase in urinary excretion of Na and/or K.

(4) The pharmaceutical composition described in any one of the above (1) to (3), wherein improvement in renal dysfunction is an increase in urine volume.

(5) The pharmaceutical composition described in any one of the above (1) to (4), wherein the pharmaceutical composition is used for improving cardiac function in heart failure and/or arrhythmia complicated by renal dysfunction.

(6) The pharmaceutical composition described in the above (5), wherein the arrhythmia is atrial fibrillation and/or atrial flutter.

(7) The pharmaceutical composition described in any one of the above (1) to (6), wherein the pharmaceutically acceptable salt is hydrochloride or citrate.

(8) The pharmaceutical composition described in any one of the above (1) to (7), wherein the renal dysfunction is acute kidney disease.

(9) The pharmaceutical composition described in any one of the above (1) to (7), wherein the renal dysfunction is chronic kidney disease.

(10) The pharmaceutical composition described in any one of the above (1) to (7), wherein the renal dysfunction is a disease selected from the group consisting of diabetic nephropathy, glomerulonephritis, renal dysfunction caused by shock or bleeding, and renal dysfunction complicated by arrhythmia or heart failure.

(11) The pharmaceutical composition described in any one of the above (1) to (10), wherein the pharmaceutical composition is used in a patient with renal dysfunction.

(12) The pharmaceutical composition described in any one of the above (1) to (11), wherein the pharmaceutical composition is used in a patient with renal dysfunction complicated by arrhythmia or heart failure.

(13) The pharmaceutical composition described in any one of the above (1) to (12), wherein the optical isomer of the 1,4-benzothiazepine-1-oxide derivative is a first optical isomer component.

(14) The pharmaceutical composition described in the above (13), wherein the optical isomer of the 1,4-benzothiazepine-1-oxide derivative is a first optical isomer component of 4-[3-(4-benzylpiperidin-1-yl)propionyl]-7-methoxy-2,3,4,5-tetrahydro-1,4-benzothiazepine-1-oxide.

(15) A method of improving renal dysfunction comprising:

a step of administering an effective dose of a pharmaceutical composition, which comprises an optical isomer of the 1,4-benzothiazepine-1-oxide derivative having the above formula [II] or a pharmaceutically acceptable salt thereof, to a subject with renal dysfunction.

(16) The method described in the above (15), wherein the subject is suffering from heart failure and/or arrhythmia complicated by renal dysfunction.

(17) The method described in the above (16), wherein the arrhythmia is atrial fibrillation and/or atrial flutter.

(18) The method described in any one of the above (15) to (17), wherein the pharmaceutically acceptable salt is hydrochloride or citrate.

(19) The method described in any one of the above (15) to (18), wherein the optical isomer of the 1,4-benzothiazepine-1-oxide derivative is a first optical isomer component.

(20) The method described in the above (19), wherein the optical isomer of the 1,4-benzothiazepine-1-oxide derivative is a first optical isomer component of 4-[3-(4-benzylpiperidin-1-yl)propionyl]-7-methoxy-2,3,4,5-tetrahydro-1,4-benzothiazepine-1-oxide.

(21) An optical isomer of the 1,4-benzothiazepine-1-oxide derivative having the above formula [II] or a pharmaceutically acceptable salt thereof, for use in improving or treating renal dysfunction.

(22) The optical isomer of the 1,4-benzothiazepine-1-oxide derivative or the pharmaceutically acceptable salt thereof for use described in the above (21), characterized in that which is for use in improving or treating renal dysfunction and improving or treating heart failure and/or arrhythmia complicated by renal dysfunction.

(23) The optical isomer of the 1,4-benzothiazepine-1-oxide derivative or the pharmaceutically acceptable salt thereof for use described in the above (22), wherein the arrhythmia is atrial fibrillation and/or atrial flutter.

(24) The optical isomer of the 1,4-benzothiazepine-1-oxide derivative or the pharmaceutically acceptable salt thereof for use described in any one of the above (21) to (23), wherein the pharmaceutically acceptable salt is hydrochloride or citrate.

(25) The optical isomer of the 1,4-benzothiazepine-1-oxide derivative or the pharmaceutically acceptable salt thereof for use described in any one of the above (21) to (24), wherein the optical isomer of the 1,4-benzothiazepine-1-oxide derivative is a first optical isomer component.

(26) The optical isomer of the 1,4-benzothiazepine-1-oxide derivative or the pharmaceutically acceptable salt thereof for use described in the above (25), wherein the optical isomer of the 1,4-benzothiazepine-1-oxide derivative is a first optical isomer component of 4-[3-(4-benzylpiperidin-1-yl)propionyl]-7-methoxy-2,3,4,5-tetrahydro-1,4-benzothiazepine-1-oxide.

(27) Use of an optical isomer of the 1,4-benzothiazepine-1-oxide derivative having the above formula [II] or a pharmaceutically acceptable salt thereof, for the production of a pharmaceutical composition for improving or treating renal dysfunction.

(28) The use described in the above (27), wherein the pharmaceutical composition is for improving or treating renal dysfunction and heart failure and/or arrhythmia complicated by renal dysfunction.

(29) The use described in the above (27), wherein the arrhythmia is atrial fibrillation and/or atrial flutter.

(30) The use described in any one of the above (27) to (29), wherein the pharmaceutically acceptable salt is hydrochloride or citrate.

(31) The use described in any one of the above (27) to (30), wherein the optical isomer of the 1,4-benzothiazepine-1-oxide derivative is a first optical isomer component.

(32) The use described in the above (31), wherein the optical isomer of the 1,4-benzothiazepine-1-oxide derivative is a first optical isomer component of 4-[3-(4-benzylpiperidin-1-yl)propionyl]-7-methoxy-2,3,4,5-tetrahydro-1,4-benzothiazepine-1-oxide.

Advantageous Effects of the Invention

The first component of the optical isomer of the 1,4-benzothiazepine-1-oxide derivative having the above formula [II] or the pharmaceutically acceptable salt thereof improves renal dysfunction. By administration of an optical isomer (compound (A)), which is an optically active 1,4-benzothiazepine-1-oxide derivative having the formula [II] and is one of optically active 4-[3-(4-benzylpiperidin-1-yl) propionyl]-7-methoxy-2,3,4,5-tetrahydro-1,4-benzothiazepine-1-oxide, as specifically shown in Examples 3 to 5 described below, a decrease in amount of blood creatinine is achieved in addition to an increase in urine volume, Na excretion, and K excretion. Moreover, the compound (A) does not cause Torsades de Pointes that is an adverse event observed in a dog with complete atrioventricular block. It is an advantageous property in clinical practice that Torsades de Pointes causes life-threatening arrhythmia but the pharmaceutical compound does not evoke the life-threatening arrhythmia.

The improvement in patients with renal dysfunction for which an effective therapeutic method has not been conventionally provided is realized by administration of the pharmaceutical composition comprising the compound (A), so that patients with renal dysfunction can be prevented from progressing to kidney failure or the number of years up to the kidney failure can be lengthened. As a result, dialysis can be avoided or the number of years up to the dialysis can be lengthened. Further, since the existing loop diuretic or thiazide diuretic has no action of improving the renal function and would rather interfere the renal function, the prognosis of a patient with renal dysfunction due to heart failure is poor; however, the renal dysfunction improving drug comprising the compound (A) having diuretic action and decreasing creatinine is evangelistic for a patient with renal dysfunction caused by heart failure or complicated by heart failure.

DESCRIPTION OF EMBODIMENTS

Figure 1:
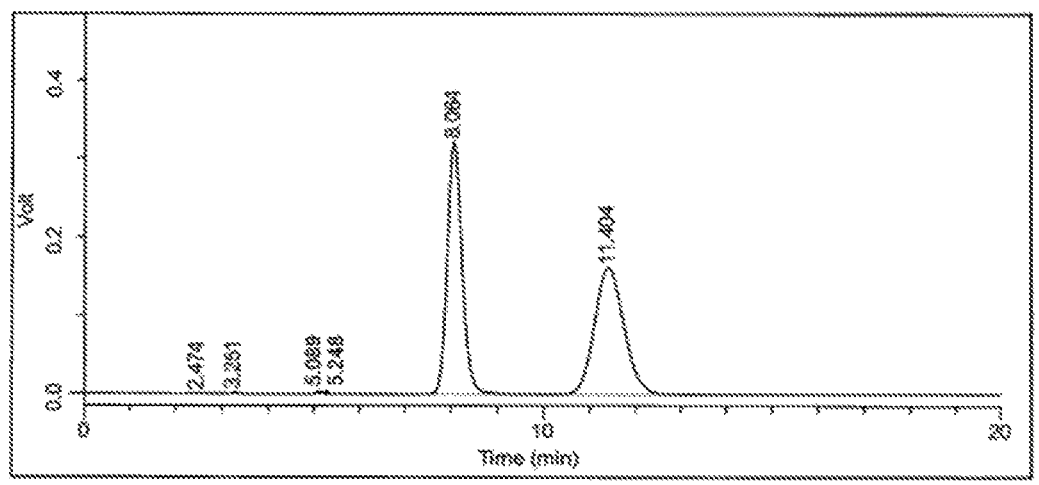
FIG. 1 illustrates an elution pattern when optically active 4-[3-(4-benzylpiperidin-1-yl)propionyl]-7-methoxy-2,3,4,5-tetrahydro-1,4-benzothiazepine-1-oxide is applied to chromatography using a chiral column. The first optical isomer component of the present invention is eluted at approximately 8.1 minutes, and the second optical isomer component as the other enantiomer thereof is eluted at approximately 11.4 minutes, showing that both the components are completely separated from each other.

According to an embodiment of the present invention, there is provided a pharmaceutical composition for improving renal dysfunction, the composition comprising an optical isomer of a 1,4-benzothiazepine-1-oxide derivative having the formula [II] or a pharmaceutically acceptable salt thereof, and a pharmaceutically acceptable carrier. Herein, as a preferred example of the optical isomer of the 1,4-benzothiazepine-1-oxide derivative, a first optical isomer component can be exemplified. Further, as a preferred example of the first optical isomer component, the optical isomer of the 1,4-benzothiazepine-1-oxide derivative is a first optical isomer component of 4-[3-(4-benzylpiperidin-1-yl)propionyl]-7-methoxy-2,3,4,5-tetrahydro-1,4-benzothiazepine-1-oxide. Herein, the first optical isomer component is an R-configured isomer. Herein, as a preferred example of the pharmaceutically acceptable salt, hydrochloride and citrate are exemplified.

According to another embodiment of the present invention, there is provided a method of improving renal dysfunction, the method comprises a step of administering an effective dose of a pharmaceutical composition, which comprises an optical isomer of the 1,4-benzothiazepine-1-oxide derivative having the above formula [II] or a pharmaceutically acceptable salt thereof, to a subject with renal dysfunction. Herein, as a preferred example of the optical isomer of the 1,4-benzothiazepine-1-oxide derivative, a first optical isomer component can be exemplified. Further, as a preferred example of the first optical isomer component, the optical isomer of the 1,4-benzothiazepine-1-oxide derivative is a first optical isomer component of 4-[3-(4-benzylpiperidin-1-yl)propionyl]-7-methoxy-2,3,4,5-tetrahydro-1,4-benzothiazepine-1-oxide. Herein, the first optical isomer component is an R-configured isomer. Herein, as a preferred example of the pharmaceutically acceptable salt, hydrochloride and citrate are exemplified.

According to still another embodiment of the present invention, there is provided an optical isomer of the 1,4-benzothiazepine-1-oxide derivative having the above formula [II] or a pharmaceutically acceptable salt thereof for use in improving or treating renal dysfunction. Herein, as a preferred example of the optical isomer of the 1,4-benzothiazepine-1-oxide derivative, a first optical isomer component can be exemplified. Further, as a preferred example of the first optical isomer component, the optical isomer of the 1,4-benzothiazepine-1-oxide derivative is a first optical isomer component of 4-[3-(4-benzylpiperidin-1-yl)propionyl]-7-methoxy-2,3,4,5-tetrahydro-1,4-benzothiazepine-1-oxide. Herein, the first optical isomer component is an R-configured isomer. Herein, as a preferred example of the pharmaceutically acceptable salt, hydrochloride and citrate are exemplified.

According to still another embodiment of the present invention, there is provided a use of an optical isomer of the 1,4-benzothiazepine-1-oxide derivative having the above formula [II] or a pharmaceutically acceptable salt thereof for producing a pharmaceutical composition for improving or treating renal dysfunction. Herein, as a preferred example of the optical isomer of the 1,4-benzothiazepine-1-oxide derivative, a first optical isomer component can be exemplified. Further, as a preferred example of the first optical isomer component, the optical isomer of the 1,4-benzothiazepine-1-oxide derivative is a first optical isomer component of 4-[3-(4-benzylpiperidin-1-yl)propionyl]-7-methoxy-2,3,4,5-tetrahydro-1,4-benzothiazepine-1-oxide. Herein, the first optical isomer component is an R-configured isomer. Herein, as a preferred example of the pharmaceutically acceptable salt, hydrochloride and citrate are exemplified.

In the present invention with each embodiment exemplified above, the renal dysfunction is acute kidney disease or chronic kidney disease, and diabetic nephropathy, glomerulonephritis, renal dysfunction caused by shock or bleeding, and renal dysfunction complicated by arrhythmia or heart failure are exemplified as a target to be treated by the present invention. In the present invention, improvement in renal dysfunction means to bring about a decrease in serum creatinine value, an increase in urinal excretion of Na and/or K, or an increase in urine volume. Further, a subject to be treated by the present invention is a subject with renal dysfunction. Herein, the target with renal dysfunction includes a target presenting with renal circulatory failure complicated by arrhythmia or heart failure. Further, the pharmaceutical composition of the present invention is also used as a pharmaceutical composition for improving a renal function and a heart function with respect to a patient with heart failure and/or arrhythmia complicated by renal dysfunction. Herein, the arrhythmia includes atrial fibrillation and/or atrial flutter.

(1) Subject for which Renal Function is Evaluated

The influence of drugs on the renal function can be examined using humans or animals. As animals, any animals such as mice, rats, guinea pigs, hamsters, dogs, cats, pigs, goats, and sheep can be used. The evaluation of the renal function can be performed by collecting urine from a human subject or an animal subject and measuring the urine volume, the amount of urinary sodium, the amount of urinary potassium, and the like. In addition, the renal function can also be evaluated by obtaining a blood sample and measuring a creatinine value in blood (serum or plasma). Further, the degree of the renal function and the renal dysfunction can be evaluated or classified by the following method.

(2) Evaluation of Renal Dysfunction

As for the evaluation of the renal dysfunction, the degree of the renal dysfunction can be evaluated by the magnitude of the glomerular filtration rate (GFR) or the like. The glomerular filtration rate in glomeruli is almost coincident with the excretion amount of creatinine per hour, that is, creatinine clearance (Ccr) so that the degree of the renal dysfunction can be evaluated by measuring the Ccr value.

The calculating formula of calculating the Ccr is as follows.

$Ccr$ (mL/min)=creatinine concentration in urine (mg/dL)×eluted rate of urine (mL/min)/creatinine concentration in serum (mg/dL)

In practical, as a simpler measurement method, in recent years, from age and the serum creatinine value, an estimated glomerular filtration rate (eGFR) is clinically and generally used.

The calculating formula of calculating the eGFR is as follows.

(Case of Male)

$eGFR = 194 \times Cr(\text{serum creatinine value})^{-1.094} \times \text{age (years)}^{-0.287}$ (Case of Female)

$eGFR = 194 \times Cr^{-1.094} \times \text{age(years)}^{-0.287} \times 0.739$ (Units are all mL/min/1.73 m$^2$)

The severity of the renal dysfunction of a human is classified, on the basis of the calculated eGFR value, into six stages shown in the following table.

TABLE 1

[Stages of renal dysfunction]

| | Classification | eGFR value |
|---|---|---|
| G1 | Normal or high | 90 or higher |
| G2 | Normal or mildly decreased | 60 to 89 |
| G3a | Mildly to moderately decreased | 45 to 59 |
| G3b | Moderately to severely decreased | 30 to 44 |
| G4 | Severely decreased | 15 to 29 |
| G5 | Kidney failure | below 15 |

The reference value table for determining whether there is a concern of renal dysfunction is also created using the serum creatinine value (Cr) as an index.

TABLE 2

[Reference values for serum creatine]

| Range | Male(mg/dL) | Female(mg/dL) |
|---|---|---|
| Caution needed/High risk | 1.6 or higher | 1.2 or higher |
| Elevated | 1.2 to 1.5 | 0.9 to 1.1 |
| Normal | 0.6 to 1.1 | 0.4 to 0.8 |

Simply, the existence of the renal dysfunction or the degree thereof can be evaluated with an elevation of the serum creatinine value (Cr).

(3) Active Ingredient of Pharmaceutical Composition of Present Invention

The active ingredient of the pharmaceutical composition of the present invention for improving renal dysfunction is the optical isomer of the 1,4-benzothiazepine-1-oxide derivative having the formula [II]. As for the optical isomer having the formula [II] of the present invention, there are mentioned a compound in a case where R in the formula [II] is a hydrogen atom and a compound in a case where R is a hydroxyl group. Examples of a preferred compound as the active ingredient of the pharmaceutical composition of the present invention include a first optical isomer component of 4-[3-(4-benzylpiperidin-1-yl)propionyl]-7-methoxy-2,3,4,5-tetrahydro-1,4-benzothiazepine-1-oxide having the following formula [IV] or a pharmaceutically acceptable salt thereof:

[Chemical Formula. 4]

[IV]

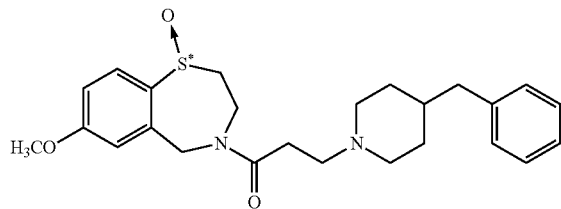

wherein, "*" symbol indicates a chiral center.

In the compound of the present invention, the bond (SO) between the sulfur atom (S) in the heterocycle and the oxygen atom (O) forms a polar atomic group showing strong electronegativity, as it is a coordination bond, to show that the bond between the sulfur atom and oxygen atom is a coordination bond, it can be described as the arrow of heterocyclic S→O, and this coordination bond can be expressed as heterocyclic $S^+$—$O^-$.

In general, if $R^1$ and $R^2$ are different from each other in a sulfoxide compound expressed by $R^1$—S(O)—$R^2$, it is known that the central chirality is present by having the sulfur atom as a chiral center. Namely, it is known that there are two types of stereoisomers, that is, a compound in which the oxygen atom is bonded from the bottom side of a horizontal plane and a compound in which the oxygen atom is bonded from the top side of a horizontal plane. Further, by ignoring the involvement of d orbital and assuming that an imaginary atom with an atomic number of 0 (zero) is bonded at the position of the electron pair of the sulfur atom, it is possible to denote either R configuration or S configuration depending on the rule of order set by R—S nomenclature.

As shown in FIG. 1, it becomes apparent that the compounds having the formula [I] include two compounds that are stably and clearly separated at a temperature of 40° C. at a ratio of approximately 1:1 by a chiral column. Further, as the collected two compounds exhibit the same behaviors according to instrumental analysis, the compounds are considered to be two types of stereoisomers based on central chirality resulting from chiral center. Further, the stereoisomer designated as the first component of the present invention is confirmed to have R configuration through crystal structure analysis.

Figure 2:
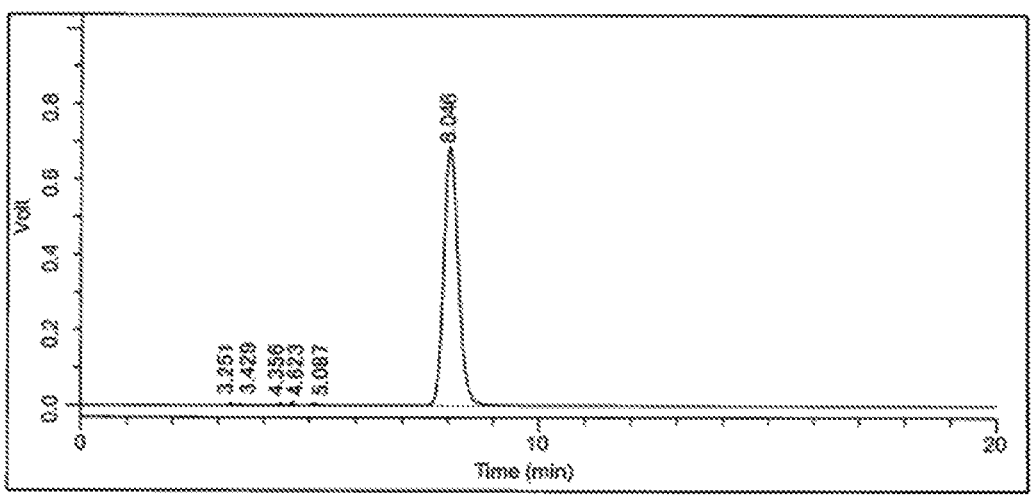
FIG. 2 illustrates an elution pattern when the collected first optical isomer component of the present invention is applied to chromatography which uses the same chiral column as the one used for resolution.
Figure 3:
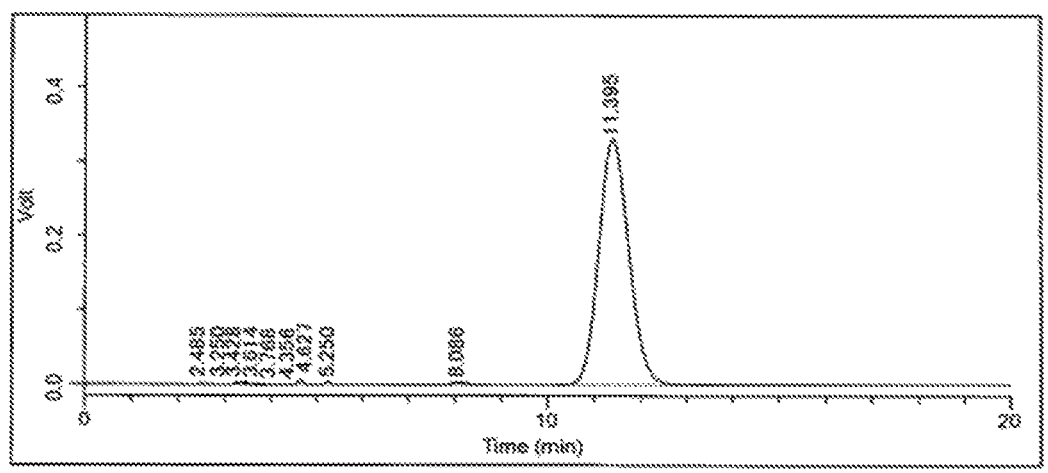
FIG. 3 illustrates an elution pattern when the second optical isomer component as the other enantiomer of the first optical isomer component of the present invention is applied to chromatography which uses the same chiral column as the one used for resolution.

In the present specification, the component eluted at 7 minutes to 9 minutes (retention time of approximately 8.1 minutes) when the compound of formula [IV] that is one of the compounds having the formula [I] is loaded onto a chiral column (CHIRALPAK AD-H (manufactured by Daicel Corporation) 0.46 cm I.D.×25 cm L.) which uses MeOH/MeCN/DEA=90/10/0.1 (v/v) as a mobile phase with a flow rate of 1.0 mL/min to elute the compound at 40° C. was referred to as the first component (or also simply referred to as the compound (A) in some cases), and the component subsequently eluted at 10 minutes to 13 minutes (retention time of approximately 11.4 minutes) was referred to as the second component (or also simply referred to as the compound (B) in some cases). As the first component and the second component can be resolved as shown in FIGS. 2 and 3 and are obviously isolated, the compound (A) as the first component is an (R)-form isomer as described above and the compound (B) as the second component is an (S)-form isomer. Incidentally, the discussion on the chiral center is also described in Patent Document 7.

(4) Salt or Solvate of Optically Active 1,4-Benzothiazepine-1-Oxide Derivative of Present Invention The 1,4-benzothiazepine-1-oxide derivative of the present invention has a basic nitrogen atom and can form an acid addition salt in this position. An acid for forming this acid addition salt is not particularly limited as long as it is a pharmaceutically acceptable salt. Preferred examples of the acid addition salt of the present invention include an inorganic acid addition salt such as hydrochloride, hydrobromide, sulfate, phosphate, or nitrate; an organic acid addition salt such as oxalate, acetate, propionate, succinate, glycolate, lactate, malate, tartrate, citrate, maleate, fumarate, methanesulfonate, benzene sulfonate, p-toluenesulfonate, or ascorbate; and an amino acid addition salt such as aspartate or glutamate. In addition, the compound of the present invention or the acid addition salt thereof may be a solvate like a hydrate.

(5) Method for Producing the First Optical Isomer Component of Optically Active 1,4-Benzothiazepine-1-Oxide Derivative of Present Invention The compound as the first component of the optical isomer of the present invention can be produced by separating the compounds having the formula [I] by a separation method using a chiral column or the like and collecting the separated compound.

The compounds having the formula [I] can be produced by oxidizing the compound having the following formula [III] by the method described in Patent Document 6:

[Chemical Formula. 3]

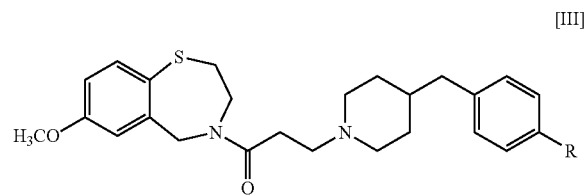

[III]

wherein, R represents a hydrogen atom or a hydroxyl group.

More specifically, for example, by oxidizing the compound having the formula [V] in the following reaction formula with a suitable oxidizing agent, an oxide having the formula [Ia] can be produced. As an oxidizing agent, a peracid, for example, peracetic acid, perbenzoic acid, meta-chloroperbenzoic acid (mCPBA), and the like can be used. As a solvent, halogenated hydrocarbon such as methylene chloride or chloroform, and the like can be used as appropriate. In order to prevent oxidation to a sulfone, the reaction temperature is preferably low temperature, for example, 0° C. to approximately 5° C. From a reaction mixture, separation and purification of a target product can be carried out by known separation and purification means such as extract operation, chromatography, or distillation.

[Chemical Formula. 5]

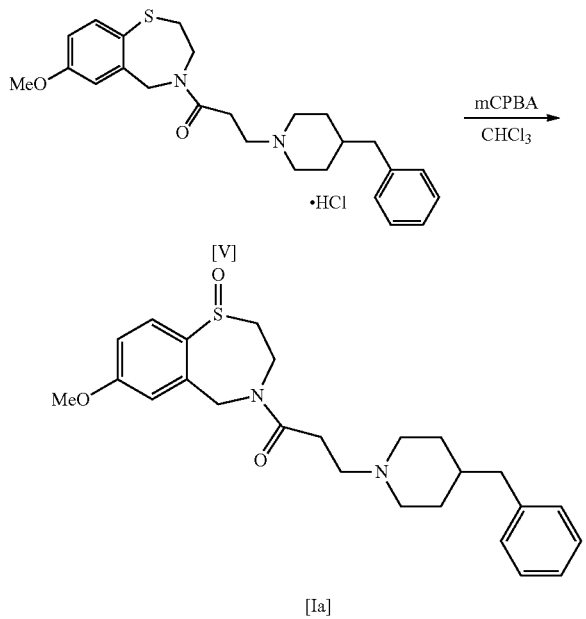

Production can be carried out by oxidizing the sulfur atom of the heterocycle of 4-[3-(4-benzylpiperidin-1-yl)propionyl]-7-methoxy-2,3,4,5-tetrahydro-1,4-benzothiazepine of the compound [V] by meta-chloroperbenzoic acid (mCPBA) as an oxidizing agent in a chloroform (CHCl$_3$) solvent.

According to the above-described reaction pathway, the 4-[3-(4-benzylpiperidin-1-yl)propionyl]-7-methoxy-2,3,4, 5-tetrahydro-1,4-benzothiazepine-1-oxide of the compound [Ia], which has been produced by oxidizing the hydrochloride of the formula [V] with meta-chloroperbenzoic acid (mCPBA) as an oxidizing agent in a chloroform solvent, is separated by silica gel chromatography using a chloroform-methanol mixture as a mobile phase, the solvent is then extracted by distillation from the separated chloroform-methanol azeotropic solvent, and the residual solvent is removed in argon to obtain a final product. The compound having the above formula [Ia], which has been obtained as described above, has a purity of 90% or more and has a molecular weight of 440.61, and the compound is an amorphous, is stable to oxygen, humidity, acid, and alkali at a room temperature, and is easily dissolved in ethanol and dimethyl sulfoxide (DMSO), and has a skin irritating property. Further, the oxalate of the compound [Ia] is a crystal which has a molecular weight of 530.65, has a purity of 90% or more and a melting point of 167 to 168° C., and this salt is soluble in water, ethanol, and dimethyl sulfoxide. It is confirmed by the measurement of the $^1$H-NMR at room temperature that the stereoisomers in an amide part exists at a ratio of approximately 2:3.

Furthermore, 4-{3-[4-(4-hydroxybenzyl)piperidin-1-yl] propionyl}-7-methoxy-2,3,4,5-tetrahydro-1,4-benzothiazepine-1-oxide, which is a compound having the formula [II] of the present invention having a hydroxyl group as R, or a pharmaceutically acceptable salt thereof can be produced by the same oxidation reaction as described above while protecting the hydroxyl group, if necessary. Furthermore, a rat or a dog is administered with the 1,4-benzothiazepine derivative, which is the parent compound, and after adding water to the obtained urine or feces followed by homogenization, the supernatant can be subjected to component separation with a retention time of 19 to 22 minutes by high performance liquid chromatography using a gradient elution, which uses reverse phase column using silica gel modified with an octadecyl group (ODS) and, as a mobile phase, water containing 0.1% trifluoroacetic acid (TFA) as a solution A and acetonitrile containing 0.1% TFA as a solution B. The separated component had a mass charge ratio (m/Z) of 457 according to mass spectrometry. Incidentally, the compound [Ia] can be also obtained by, according to the same method as above, the component separation with a retention time of 27 to 30 minutes by high performance liquid chromatography using a gradient elution.

Further, it is also possible to consider a method for producing a compound of the formula [II] of the present invention by oxidizing 7-methoxy-2,3,4,5-tetrahydro-1,4-benzothiazepine by the same method as above to obtain 7-methoxy-2,3,4,5-tetrahydro-1,4-benzothiazepine-1-oxide, separating a stereoisomer therefrom by a chiral column, collecting one enantiomer, and carrying out amidation of the enantiomer at suitable reaction conditions.

(6) Administration Form of Pharmaceutical Composition of Present Invention

The first optical isomer component of the compound having the formula [II] of the present invention or the salt thereof has actions of increasing the urine volume, increasing the amount of urinary sodium, increasing the amount of urinary potassium, and/or reducing the amount of serum creatinine and has an improving effect with respect to the renal function.

Therefore, the first optical isomer component of the compound having the formula [II] of the present invention or the salt thereof can be used as an active ingredient of the pharmaceutical composition. The pharmaceutical composition of the present invention can be administered through oral administration, transmucosal administration, percutaneous administration, intravenous infusion, or the like.

(7) Dosage Form and Formulation of Pharmaceutical Composition of Present Invention In a case where the pharmaceutical composition of the present invention is prepared as a solid composition for oral administration, it is possible to have a dosage form such as a tablet, a pill, powder, or a granule form. In such a solid composition, one or more of the active ingredients are mixed with at least one inactive diluent agent, dispersing agent, adsorbent, or the like, for example, lactose, mannitol, glucose, hydroxypropyl cellulose, microcrystalline cellulose, starch, polyvinylpyrrolidone, magnesium aluminometasilicate, silicic anhydride powder, or the like, and the solid composition can be produced according to a conventional method.

In a case where the pharmaceutical composition of the present invention is prepared as a tablet or a pill, coating may be carried out with a membrane of stomach-soluble or intestine-soluble film consisting of white sugar, gelatin, hydroxypropyl-cellulose, or hydroxymethylcellulose phthalate, or the like, and the coating may be carried out to have two or more layers. Furthermore, the pharmaceutical composition may be prepared as a capsule such as gelatin or ethylcellulose.

In a case where the pharmaceutical composition of the present invention is prepared as a liquid composition for oral administration, it is possible to have dosage forms such as pharmaceutically acceptable emulsions, solutions, suspensions, syrups, or elixir agents. As a diluent agent to be used, for example, purified water, ethanol, vegetable oil, an emulsifier, or the like is mentioned. Alternatively, the composition may be mixed with adjuvants such as permeation agents, suspending agents, sweetening agents, flavoring agents, aromatic agents, or antiseptic agents other than the diluent agents.

In a case where the pharmaceutical composition of the present invention is prepared as an injection solution for parenteral administration, sterile and aqueous or non-aqueous solution agents, solubilizing agents, suspensions, or emulsifiers are used. As aqueous solution agents, solubilizing agents, and suspensions, for example, there are water for injection, distilled water for injection, physiological saline, cyclodextrin and a derivative thereof, organic amines such as triethanolamine, diethanolamine, monoethanolamine, or triethylamine, or inorganic alkali solutions, and the like.

In a case where the pharmaceutical composition of the present invention is prepared as a water-soluble solution, for example, propylene glycol, polyethylene glycol, vegetable oil like olive oil, alcohols like ethanol, or the like may be used. Alternatively, as a solubilizing agent, for example, surfactants (for forming mixed micelle) such as polyoxyethylene hydrogenated castor oil or sucrose fatty acid ester, lecithin or hydrogenated lecithin (for forming liposome), or the like is also used. Alternatively, it is also possible to prepare emulsion agents which consists of non-water soluble solubilizing agents such as vegetable oil, and lecithin, polyoxyethylene hydrogenated castor oil, polyoxyethylene polyoxypropylene glycol or the like.

As dosage forms for parenteral administration, percutaneous absorption drugs such as a patch can also be employed. In a case where the pharmaceutical composition of the present invention is prepared as an external preparation for skin such as a patch, the pharmaceutical composition can be prepared in any form such as aqueous system, solubilized system, emulsified system, powder-dispersed system, water-oil two-layer system, or water-oil-powder three-layer system. Since the compound (A) is water-soluble, the compound (A) can be preferably mixed by being dissolved in water or being dissolved in water and then being emulsified in preparation, but the preparation method is not limited thereto. As for an external preparation for skin, components, which are mixed with a general pharmaceutical composition in the range that the effect of the present invention is not impaired, for example, alcohols, oil components, surfactants, ultraviolet absorbers, humectants, thickeners, antiseptic agents, inorganic powder, organic powder, perfume materials, and the like can be arbitrarily mixed. Further, in a case where the pharmaceutical composition of the present invention is prepared as an external preparation for skin such as an ointment, the external preparation for skin such as an ointment can be prepared by dissolving or dispersing the compound (A) in a lipophilic, water-soluble, or emulsion-type base. Examples of the base include vaseline, lanolin, and polyethylene glycol, but the base is not particularly limited.

In a case where the route of administration is transmucosal, for example, a dosage form such as a sublingual tablet may be used. The production of the sublingual tablet can be performed, for example, by tableting at a lower pressure than that in the case of a general tablet in a general method for producing a tablet. Other than, transmucosal dosage forms such as a suppository, an enteric tablet, and an enteric-coated capsule are also employed as appropriate by formulation by a general method.

(8) Dosage Amount of Pharmaceutical Composition of Present Invention

The compound having the formula [II] of the present invention or the salt thereof is administered as a free compound to have a blood concentration of 10 to 3000 ng/mL, preferably 20 to 1500 ng/mL, and more preferably 30 to 1000 ng/mL, although it may vary depending on age, body weight, symptom, a therapeutic effect, an administration method, a treatment time, or the like. The blood concentration immediately after administration is preferably 300 ng/mL or more. In order to realize such a blood concentration, for example, the compound or the salt thereof can be generally administered once daily or divided into several times per day and either orally or parenterally, within a range of 0.1 mg to 1 g, preferably 1 mg to 1 g, or 0.1 mg to 0.5 g per an adult per day. The compound having the formula [II] of the present invention that is an active ingredient of the pharmaceutical composition of the present invention is preferably a first optical isomer component of the compound having the formula [II]. More preferably, the compound is a first optical isomer component (compound (A)) of optically active 4-[3-(4-benzylpiperidin-1-yl)propionyl]-7-methoxy-2,3,4,5-tetrahydro-1,4-benzothiazepine-1-oxide.

(9) Medicinal Use of Pharmaceutical Composition of Present Invention

The pharmaceutical composition of the present invention can be used for symptomatic improvement or treatment of diseases accompanied by renal dysfunction.

The diseases accompanied by renal dysfunction are also classified, on the basis of clinical conditions or affected regions thereof, into glomerular diseases, tubulointerstitial diseases, kidney failure, nephropathy, polycystic kidney diseases, and the like. The glomerular diseases include diseases accompanied by glomerular dysfunction such as acute nephritic syndrome, rapidly progressive glomerulonephritis syndrome, recurrent or persistent hematuria, chronic nephritic syndrome, and nephrotic syndrome. The tubulointerstitial diseases include diseases accompanied by renal tubulointerstitial damage such as tubulointerstitial nephritis (acute, chronic, or unspecified tubulointerstitial nephritis).

The kidney failure includes acute renal failure and chronic renal failure. The nephropathy includes virus nephropathy (HB virus-associated nephropathy, HC virus-associated nephropathy, HIV-associated nephropathy, BK virus-associated nephropathy, or the like), renal sarcoidosis, diabetic nephropathy, hereditary nephropathy, familial nephritis, hypertensive nephropathy, hepatorenal syndrome, NSAID nephropathy, analgesic nephropathy, contrast nephropathy, nephropathy induced by heavy metals, and the like. All of these diseases may be targets for which the pharmaceutical composition of the present invention is used. As for the renal dysfunction, any diseases of acute diseases or chronic diseases are targets for which the pharmaceutical composition of the present invention is used. In addition, as a preferred use application of the pharmaceutical composition of the present invention, diabetic nephropathy, glomerulonephritis, renal dysfunction caused by shock or bleeding, and renal dysfunction complicated by arrhythmia or heart failure can be exemplified.

EXAMPLES

Hereinafter, the present invention will be described in more detail by means of Examples, but the present invention is not limited by these examples at all.

Example 1

Production of 4-[3-(4-benzylpiperidin-1-yl)propionyl]-7-methoxy-2,3,4,5-tetrahydro-1,4-benzothiazepine-1-oxide of Compound of Formula [Ia]

In a reaction vessel, 30.0 g of 4-[3-(4-benzylpiperidin-1-yl)propionyl]-7-methoxy-2,3,4,5-tetrahydro-1,4-benzothiazepine hydrochloride of the compound having the above formula [V] was added, 800 mL of chloroform ($CHCl_3$) as a solvent was added thereto, and dissolved under stirring at room temperature. Subsequently, the reaction mixture was cooled by immersing the reaction vessel in an ice-cold water bath so that the temperature inside the vessel became 0 to 1° C. 600 mL of chloroform ($CHCl_3$) solution dissolved with 14.0 g of meta-chloroperbenzoic acid (mCPBA) was gradually added dropwise thereto with a dropwise addition time of 110 minutes while being careful not to have an increase of the reaction temperature. After completion of the dropwise addition, stirring was performed at 0 to 1° C. for approximately 20 minutes.

Subsequently, $H_2O$ solution (200 mL) dissolved with 4.14 g of $Na_2SO_3$ was added dropwise thereto at 0 to 5° C. over 1 minute, and after completion of the dropwise addition, stirring was performed at 0 to 5° C. for 10 minutes. Subsequently, while maintaining the reaction mixture cool at 0 to 5° C., 1 mol/liter aqueous solution of NaOH was added dropwise thereto over 1 minute. After the dropwise addition, stirring was performed at 0 to 5° C. for 15 to 20 minutes. After separating out the organic layer, the aqueous layer was extracted with 600 mL of $CHC_3$. The organic layer was combined with extracts and washed once with 200 mL of $H_2O$ and once with 200 mL of saturated NaCl solution. The organic layer was dried with anhydrous $Na_2SO_4$, and then concentrated in vacuo.

By the silica gel chromatography, concentrated residue was eluted by ethanol for purification. A target compound was obtained at 13 g as an amorphous to viscous oil phase.

IR ($c^{-1}$): 3452, 2919, 1643, 1594, 1022

$^1$H-NMR ($CDCl_3$ 300 MHz): δ
1.1-2.95 (17H, m), 3.78 (3H, s), 3.86-4.16 (2H, m), 4.65 (2H, s), 6.8-7.65 (8H, m) MS (FD-MS):441 ($M^+$)

Example 2

The first optical isomer component and the second optical isomer component of the compound of the formula [IV] of the present invention were prepared by separating the compound of the formula [Ia], which had been produced in Example 1, and then by collecting the separated components, at the conditions described below.

Column: CHIRALPAK AD-H (manufactured by Daicel Corporation)
Size: 0.46 cm I.D.×25 cm L.
Mobile phase: MeOH/MeCN/DEA=90/10/0.1 (v/v)
Flow rate: 1.0 mL/min
Temperature: 40° C.
Detection wavelength: 245 nm
Injection amount: 10 μL
MeOH represents methanol, MeCN represents acetonitrile, and DEA represents diethylamine, respectively.
Meanwhile, as for the devices, the followings were used.
Pump: LC-20AD (manufactured by SHIMADZU CORPORATION)
Detector: SPD-20A (manufactured by SHIMADZU CORPORATION)
Auto sampler: SIL-20A (manufactured by SHIMADZU CORPORATION)

From 10 g of the compound having the formula [Ia], it was possible to collect the first optical isomer component and the second optical isomer component, each in an amount of 4 g.

Each of the collected components was applied to column chromatography at the same conditions as described above. The results are shown in FIGS. 2 and 3, respectively.

Example 3

Action on dog renal function by administration of the first optical isomer component (compound (A)) of formula [IV] of present invention The influence of the compound (A) of the present invention on the renal function was examined.

Method: 5 mg/kg of ketamine hydrochloride (KETALAR FOR INTRAMUSCULAR INJECTION 500 mg, 50 mg/mL, DAIICHI SANKYO COMPANY, LIMITED) was intramuscularly administered to a 10 to 12 kg beagle dog (n=4) as a preanesthetic administration, and then anesthesia was performed by inhale of isoflurane. After intratracheal intubation, isoflurane was inhaled in a range of 1 to 5%, artificial ventilation was carried out, and a tracheal tube was intubated and mounted on a ventilator. The examinations were performed under the ventilation conditions of 10 to 25 mL/kg/stroke and 10 to 20 stroke/min. The lower abdomen was incised, the dog was cannulated in the ureters at the both sides, and urine was continually collected. After the urination became constant, the compound (A) as the first optical isomer component which had been obtained in Example 2 was dissolved in physiological saline, and cumulative doses of 0.1 mg/kg, 0.3 mg/kg, 1 mg/kg, and 3 mg/kg of Compound (A) were administered through the leg veins for 20 minutes each.

A blood sample was obtained before the start of administration of the compound [IV] and every 20 minutes after completion of administration beginning at a time immediately after completion of administration (0 minutes), and changes in urine volume from the ureters at the both sides, Na in urine, K in urine, and a serum creatinine value were examined every 20 minutes. Whether a significant difference between values after the administration of 1 mg/kg or 3 mg/kg and the control was recognized was examined with paired t. $P<0.05$ was considered to be a significant difference.

Figure 4:
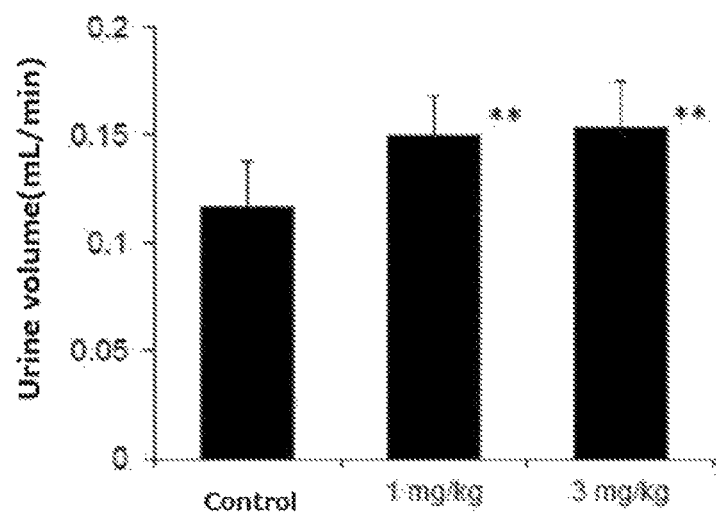
FIG. 4 illustrates an influence of the first optical isomer component (compound (A)) of 4-[3-(4-benzylpiperidin-1-yl)propionyl]-7-methoxy-2,3,4,5-tetrahydro-1,4-benzothiazepine-1-oxide on the urine volume of dog. The compound (A) increases urine volume in a dose-dependent manner. In the drawing, the significant difference at $p<0.01$ is indicated by "**".

Result and discussion: The influence of the compound (A) that is the first optical isomer component of the compound of the formula [IV] of the present invention on the urine volume is shown in FIG. 4. After the administration of 1 mg/kg and 3 mg/kg, as compared to the control, a significant increase in urine volume was recognized. Further, a dose-dependent tendency was recognized in an increase in urine volume.

Figure 5:
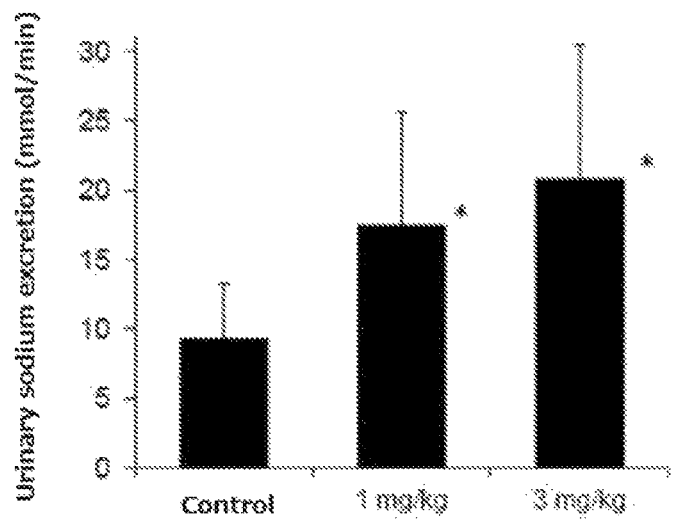
FIG. 5 illustrates an influence of the compound (A) on excretion of Na in dog urine. The compound (A) increases urinary Na excretion in a dose-dependent manner. In the drawing, the significant difference at $p<0.05$ is indicated by "*".

The influence of the compound (A) that is the first optical isomer component of the compound of the formula [IV] of the present invention on the excretion of sodium (the amount of urinary sodium) is shown in FIG. 5. After the administration of 1 mg/kg and 3 mg/kg, as compared to the control, a significant increase in excretion amount of sodium was recognized. Further, a dose-dependent tendency was recognized in an increase in excretion amount of sodium.

Figure 6:
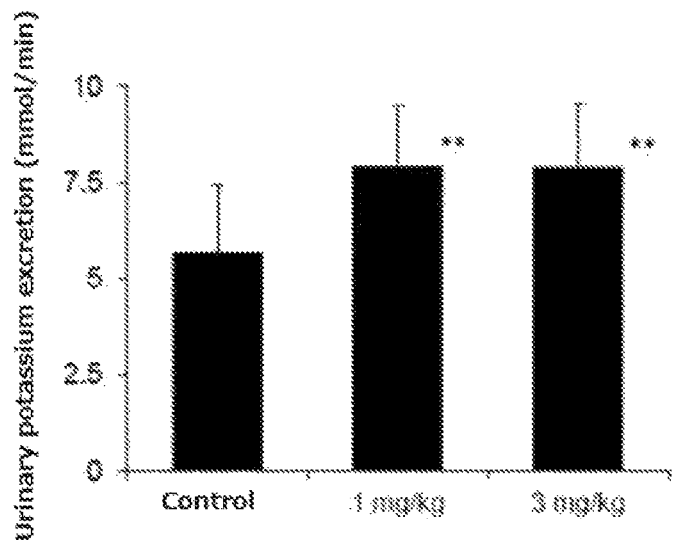
FIG. 6 illustrates an influence of the compound (A) on excretion of K in dog urine. The compound (A) increases urinary K excretion in a dose-dependent manner. In the drawing, the significant difference at $p<0.01$ is indicated by "**".

The influence of the compound (A) that is the first optical isomer component of the compound of the formula [IV] of the present invention on the excretion of potassium (the amount of urinary potassium) is shown in FIG. 6. After the administration of 1 mg/kg and 3 mg/kg, as compared to the control, a significant increase in excretion amount of potassium was recognized.

Figure 7:
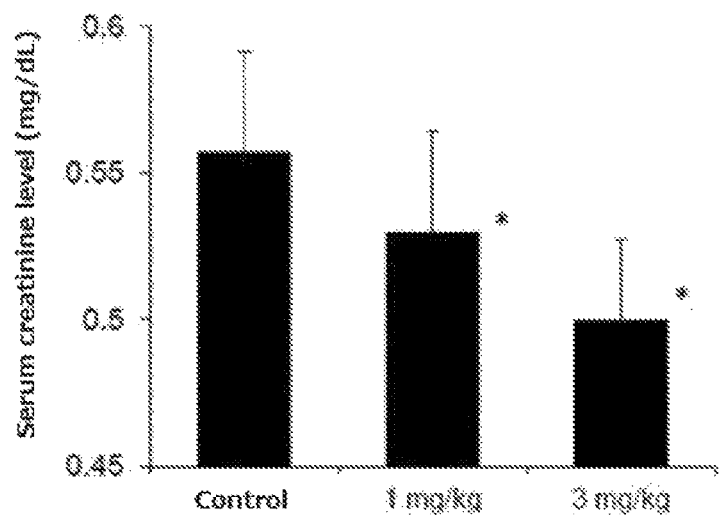
FIG. 7 illustrates an influence of the compound (A) on a serum creatinine value in dogs. The compound (A) reduces serum creatine level in a dose-dependent manner. In the drawing, the significant difference at $p<0.05$ is indicated by "*".

The influence of the compound (A) that is the first optical isomer component of the compound of the formula [IV] of the present invention on the serum creatinine value is shown in FIG. 7. After the administration of 1 mg/kg and 3 mg/kg, as compared to the control, a significant decrease in serum creatinine value was recognized. A dose-dependent tendency was recognized in a decrease in serum creatinine value.

Example 4

Action on rat, ischemia/reperfusion injury by administration of first optical isomer component (compound (A)) of formula [IV] of present invention The action of the compound (A) of the present invention on ischemia/reperfusion injury in kidneys was examined.

Method: Eleven 8-week-old male SD rats were used and laparotomized under anesthesia, the renal artery of the left kidney, and then after 1 minute, that of the right kidney were clamped using a non-traumatic clip for 45 minutes, and then reperfusion was performed.

The hydrochloride of the first optical isomer component (compound (A)) of the formula [IV] of the present invention was dissolved in physiological saline, and 4 mg/kg (before ischemia) and 2 mg/kg (before and after reperfusion) of the compound (A) (6 mg/kg in total) were administered for 10 minutes before ischemia and before and after reperfusion, respectively. On the other hand, the placebo group was subjected to the same procedure as in the compound (A)—administration group in every way except that only physiological saline was administered instead of physiological saline solution of the hydrochloride of the compound (A). Each experiment was performed with n=5 for the first group (placebo group) and with n=6 for the second group (compound (A) group), and the results are compared between the groups.

For calculation of a creatinine clearance value, the total urine of during 60 minutes before administration and during 0 to 8, 8 to 24, and 24 to 48 hours after administration were collected in each rat, and the urine volume and the value of creatinine in urine were measured. Further, a blood sample was obtained before administration and after 4, 8, 24, and 48 hours of administration and serum creatinine values were measured over time. The creatinine clearance values were obtained from the urine volume and the values of creatinine in urine and plasma which had been obtained by these measurements.

By Dunnett test, $P<0.05$ was considered to be a significant difference.

Figure 8:
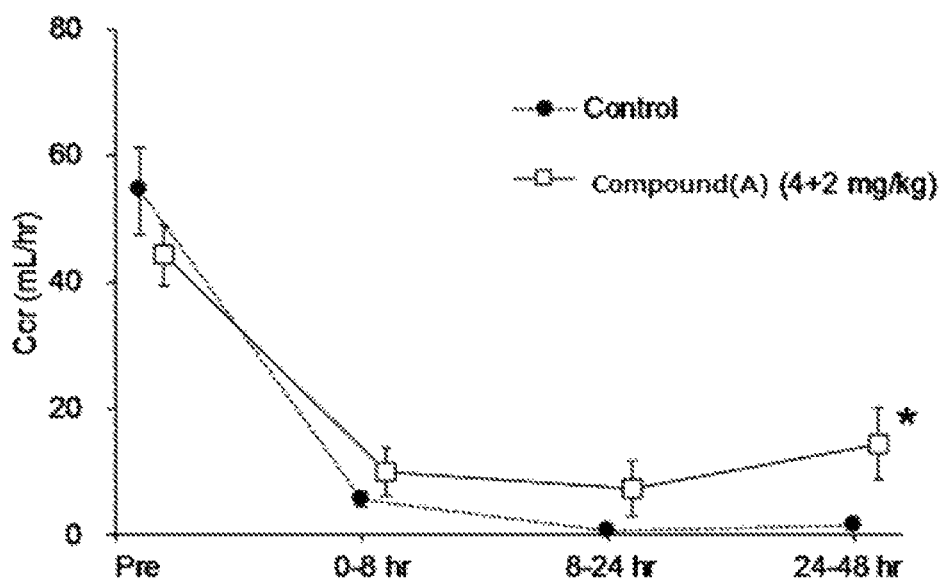
FIG. 8 illustrates an influence of the compound (A) on creatinine clearance in experimental model of ischemia/reperfusion injury in rats. The compound (A) significantly improves creatinine clearance at 24 to 48 hours after ischemia/reperfusion. In the drawing, the significant difference at $p<0.05$ is indicated by "*".

Result and discussion 1: The influence of the compound (A) on creatinine clearance in a rat ischemia/reperfusion injury experiment was shown in FIG. 8.

The creatinine clearance values before administration of the first group and the second group were 54.5±6.9 and 44.2±4.7 mL/hr, respectively.

At 24 to 48 hours after administration, the creatinine clearance value of the first group was 1.6±0.4 mL/hr so that heavy renal dysfunction was recognized; however, the creatinine clearance value of the second group was 14.5±5.6 mL/hr so that a significant improvement in creatinine clearance was recognized in the compound (A) group as compared to the placebo group.

As described above, the compound (A) significantly improved a decrease in creatinine clearance caused by ischemia/reperfusion injury.

Figure 9:
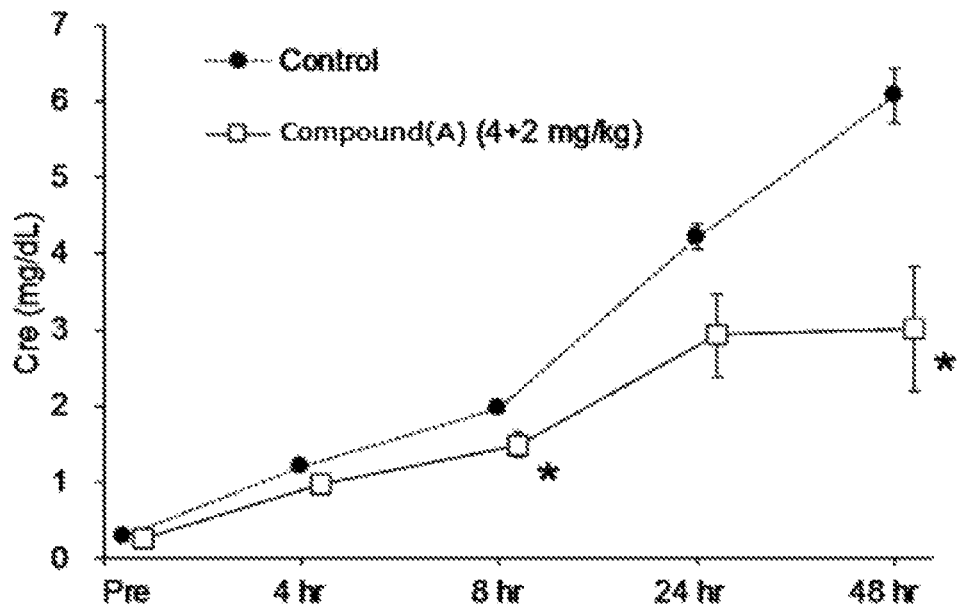
FIG. 9 illustrates an influence of the compound (A) on a serum creatinine value in experimental model of ischemia/reperfusion injury in rats. The compound (A) significantly reduces serum creatinine level. In the drawing, the significant difference at $p<0.05$ is indicated by "*".

Result and discussion result 2: The influence of the compound (A) on serum creatinine value in an experimental model of ischemia/reperfusion injury in rats was shown in FIG. 9.

The serum creatinine values of the first group and the second group before administration were 0.29±0.01 and 0.27±0.01 mg/dL, respectively.

The serum creatinine values of the first group and the second group at 48 hours after administration were 6.07±0.36 mg/dL and 3.02±0.82 mg/dL, respectively, and the serum creatine value of the compound (A) group was a significantly lower value than that of the placebo group. Further, in the serum creatinine values at 8 hours after administration, a significant difference between the compound (A) group and the placebo group was recognized.

As described above, the compound (A) significantly improved an increase in serum creatinine value caused by ischemia/reperfusion injury.

Example 5

Action on human renal function by administration of first optical isomer component (compound (A)) of formula [IV] of present invention After an adult (male) was caused to completely urinate before administration of the compound (A), the compound (A) was administered to the adult (male). The study was performed in a double-blinded manner.

Method: Three groups including a group with 0 mg/kg of the compound (A) being administered (placebo group: 8 persons), a group with 0.05 mg/kg of the compound (A) being administered (6 persons), and a group with 0.15 mg/kg of the compound (A) being administered (6 persons) were made. The hydrochloride of the compound (A) was dissolved in physiological saline and intravenously administered at a rate of 2.5 mL/min for 20 minutes. The urine volume from a time immediately after administration to a time after 8 hours of administration and the maximum plasma concentration immediately after administration were measured.

Figure 10:
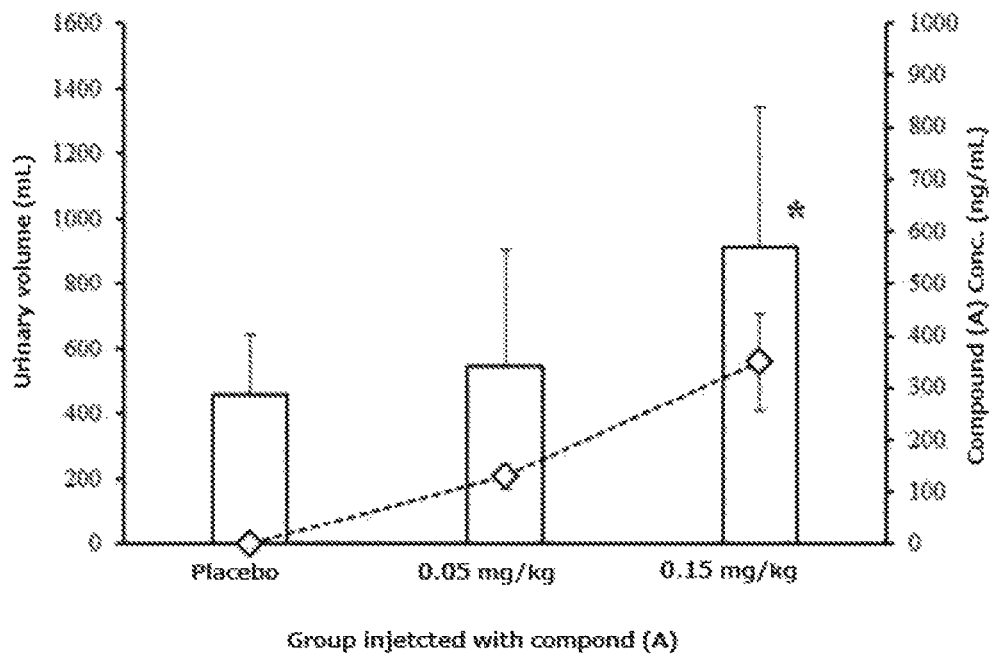
FIG. 10 illustrates the concentration of the compound (A) in blood and 8-hour urine volume from immediately after to 8 hours after administration in the case of compound (A) administration in adult human. The urine volume is shown by the height of the bar along with the standard deviation. The concentration of the compound (A) in plasma is expressed with an open diamond (◊) and is shown along with the standard deviation. The significant difference at $p<0.05$ is indicated by "*".

Result and discussion: Measurement values of the urine volume from a time immediately after administration to a time after 8 hours of administration and the maximum plasma concentration immediately after administration are shown in FIG. 10. The total urine volume from 0 to 8 hours after administration were 459.8 (±184.1) mL in the placebo group, 545.2 (±362.1) mL in the group with 0.05 mg/kg of the compound (A) being administered, and 914.2 (±431.0) mL in the group with 0.15 mg/kg of the compound (A) being administered. In the group with 0.15 mg/kg of the compound (A) being administered, a significant (p<0.05) increase in urine volume was recognized as compared to the placebo group. In the group with 0.15 mg/kg of the compound (A) being administered, the urine volume was increased approximately two times that of the placebo group.

The blood concentration of the compound (A) immediately after administration was 349.3±93.7 ng/mL in the group with 0.15 mg/kg of the compound (A) being administered. From this results, it became apparent that the compound (A) increases the urine volume also in humans.

In the group with 0.05 mg/kg of the compound (A) being administered, since a significant (p<0.05) increase in urine volume was not recognized as compared to the placebo group, it is considered that it is desirable to administer the compound (A) at a dose that achieves 300 ng/mL or more and more preferably 300 ng/mL or more, for example, 300 ng/mL to 1500 ng/mL and preferably 350 ng/mL to 1000 ng/mL at immediately after administration.

INDUSTRIAL APPLICABILITY

The present invention provides a pharmaceutical composition which has actions of increasing the urine volume, increasing the amount of urinary sodium, increasing the amount of urinary potassium, and/or decreasing the amount of serum creatinine and is useful for improving renal dysfunction, and the pharmaceutical composition is useful in pharmaceutical and medical fields and has industrial applicability.

The invention claimed is:

1. A method of improving renal dysfunction comprising: a step of administering an effective dose of a pharmaceutical composition, which comprises an optical isomer of the 1,4-benzothiazepine-1-oxide derivative having the following formula [II] or a pharmaceutically acceptable salt thereof, to a subject with renal dysfunction and without a complication with cardiac disorders:

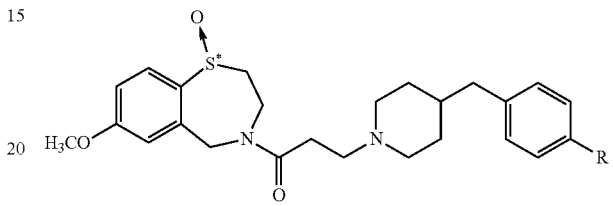

[II]

wherein R represents a hydrogen atom or a hydroxyl group, and "*" indicates the presence of optical isomers.

2. The method according to claim 1, wherein the pharmaceutically acceptable salt is hydrochloride or citrate.

3. The method according to claim 1, wherein the optical isomer of the 1,4-benzothiazepine-1-oxide derivative is a first optical isomer component.

4. The method according to claim 3, wherein the optical isomer of the 1,4-benzothiazepine-1-oxide derivative is a first optical isomer component of 4-[3-(4-benzylpiperidin-1-yl)propionyl]-7-methoxy-2,3,4,5-tetrahydro-1,4-benzothiazepine-1-oxide.

5. The method according to claim 4, wherein the first optical isomer component of 4-[3-(4-benzylpiperidin-1-yl)propionyl]-7-methoxy-2,3,4,5-tetrahydro-1,4-benzothiazepine-1-oxide is an (R)-form isomer.

* * * * *